United States Patent [19]

Hagen et al.

[11] Patent Number: 4,841,966

[45] Date of Patent: Jun. 27, 1989

[54] ELECTRODE CONSISTING OF AT LEAST THREE ELEMENTS USEFUL FOR A HF SURGICAL INSTRUMENT

[75] Inventors: Uwe Hagen, Forchheim; Udo Redler, Effeltrich, both of Fed. Rep. of Germany

[73] Assignee: Siemens Aktiengesellschaft, Berlin and Munich, Fed. Rep. of Germany

[21] Appl. No.: 158,519

[22] Filed: Feb. 22, 1988

[30] Foreign Application Priority Data

Sep. 11, 1987 [DE] Fed. Rep. of Germany ....... 3730603

[51] Int. Cl.⁴ ............................................. A61B 17/39

[52] U.S. Cl. ............................... 128/303.13; 128/798; 128/908

[58] Field of Search ...................... 128/303.13, 303.14, 128/303.17, 639–641, 643, 644, 798, 802, 803, 908

[56] References Cited

U.S. PATENT DOCUMENTS

| | | | |
|---|---|---|---|
| 3,380,445 | 4/1968 | Frasier | 128/639 |
| 3,386,445 | 6/1968 | McDonald | 128/798 |
| 3,960,141 | 6/1976 | Bolduc | 128/303.13 X |
| 4,082,086 | 4/1978 | Page et al. | 128/640 |
| 4,362,164 | 12/1982 | Little et al. | 128/639 |
| 4,381,789 | 5/1983 | Naser et al. | 128/798 |

FOREIGN PATENT DOCUMENTS

| | | | |
|---|---|---|---|
| 1219642 | 3/1987 | Canada . | |
| 3509975 | 10/1986 | Fed. Rep. of Germany | 128/640 |
| 3544443 | 6/1987 | Fed. Rep. of Germany . | |

OTHER PUBLICATIONS

Medical & Biological Engineering & Computing, vol. 24, No. 3, May 1986, pp. 311–316, "Modelling of Thermal Patterns of Electrosurgical Dispersive Electrodes", Aubry–Frize et al.

*Primary Examiner*—Lee S. Cohen

*Attorney, Agent, or Firm*—Lawrence C. Edelman

[57] ABSTRACT

An electrode of at least three elements, useful in particular as a neutral electrode for a high frequency surgical instrument. The electrode elements are placed on a common flexible carrier and are arranged symmetrically and rotationally displaced from each other with respect to an axis of symmetry which extends perpendicular from the carrier. Thus, application of the electrode to a patient with respect to an axis of rotation on the patient is not critical and safe monitoring of proper contact on the patient is ensured.

4 Claims, 1 Drawing Sheet

12a
22
14a
11
21
A
24
10
26
16a

ELECTRODE CONSISTING OF AT LEAST THREE ELEMENTS USEFUL FOR A HF SURGICAL INSTRUMENT

BACKGROUND OF THE INVENTION

1. Field of the Invention

The invention relates to an electrode consisting of at least three elements, and in particular to a neutral electrode for a High Frequency (HF) surgical instrument in which the electrode elements are arranged on a common flexible carrier.

2. Description of the Prior Art

A neutral electrode of the above mentioned kind which includes three planar electrode elements is known, for example, from U.S. patent application Ser. No. 929,561 filed Nov. 10, 1986 (corresponding with the present Assignee's German Patent Publication DE-OS No. 35 44 443), now U.S. Pat. No. 4,754,757.

In connection with HF surgical instruments it has been found that a multiple element design for the neutral electrode is desirable if the intent is to ascertain with a monitor circuit whether, during the HF surgical procedure, the neutral electrode is in contact with the patient over a large area and not only in some points. Such a monitor circuit for a three-element neutral electrode is shown in FIG. 4 of the above-mentioned DE-OS No. 35 44 443 and described in greater detail in the related text.

If a multi-element planar electrode having rectangular electrode elements is used and if this planar electrode is applied on the thigh of a patient, two application directions, in principle, are possible. In one application direction the three electrode elements are aligned in the direction of the longitudinal axis of the thigh. This case should be called one of improper application, for the high frequency going out from the surgical field, for example in the abdominal area, will reach the three electrode elements with different intensities. With respect to monitoring the proper contact of the neutral electrode with the patient, this can lead to erroneous measurements. In the other case, the three electrode elements are applied transversely to the longitudinal direction of the thigh. This case can be referred to as one of proper application, because in this case, the three electrode elements are reached by the high frequency going out from the surgical field approximately with the same intensity, given identical surface areas.

In hospitals, the application of the neutral electrode is frequently carried out by auxiliary personnel. In order to avoid the possibility of committing an error and, hence, loss of time in preparing a patient for the surgical procedure, a possible solution should be sought as to how the individual electrode elements, independently of the orientation of the neutral electrode with respect to the longitudinal axis of, for example, the thigh, can be impressed with the same HF intensity (power). As a first approximation it should be assumed that all of the electrode elements have the same surface area.

An object of the invention, therefore, is to develop an electrode of at least three elements so that a substantially uniform distribution of the high frequency energy going out from the surgical field onto the electrode elements is achieved. In this connection it is basically irrelevant in which orientation with respect to its normal the neutral electrode is applied on the patient.

SUMMARY OF THE INVENTION

This problem is solved by the invention wherein the neutral electrode elements are arranged symmetrically with respect to an axis of symmetry which is perpendicular on the electrode carrier and, with respect to the axis of symmetry, displaced in a circumferential direction.

In order to achieve easy application, each electrode element should have at least partially curved edges. The electrode elements can be,in particular, round, but can also be sector-shaped.

In the general case one will proceed with the electrode elements being of identical surface area. In special cases it may, however, be best to build one or the other electrode elements of a different size. This will depend on the geometric configuration.

Other features and advantages of the invention will be apparent from the description of the preferred embodiments, and from the claims.

For a fuller understanding of the present invention, reference should now be made to the following detailed description of the preferred embodiments of the invention and to the accompanying drawings.

DETAILED DESCRIPTION OF THE PREFERRED EMBODIMENTS

Figure 1:
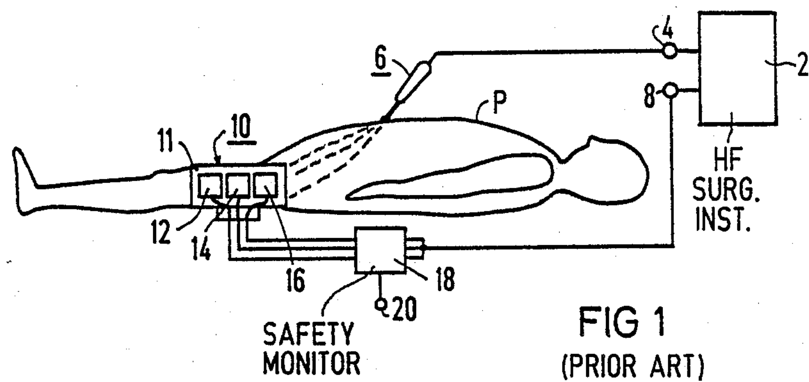
FIG. 1 illustrates an improper application of a neutral electrode on a patient according to the state of the art.

According to FIG. 1 an HF instrument 2 comprises a connection 4 for an active electrode 6 and a further connection 8 for a neutral electrode 10, which is shown fastened to the thigh of a patient P. The neutral electrode 10 is, in the present case, subdivided into three electrode elements 12, 14, and 16. During the operation the surgeon guides active electrode 6 and carries out directed coagulations or sections upon patient P.

A circuit arrangement 18 is associated with HF surgical instrument 2 for monitoring neutral electrode 10. Circuit arrangement 18 is a safety circuit, which permits determination of whether neutral electrode 10 is in contact with the patient P over a sufficiently large area so as to allow proper operation of the HF surgical apparatus. If this is not the case, it transmits a warning signal at an output 20. Safety circuit 18 can be built according to the techniques shown in the forenoted United States Patent Application, incorporated herein by reference.

In FIG. 1 it is assumed that electrode elements 12, 14 and 16 have rectangular cross sections and are arranged on a carrier 11 in the longitudinal direction of the patients thigh. In this case, upon turn-on HF surgical instrument 2, no uniform distribution of the HF energy onto three electrode elements 12, 14 and 16 can be expected. As a consequence of this unsymmetrical flow through electrode elements 12, 14 and 16 of the HF energy, reliable monitoring of the proper contact of neutral electrode 10 is potentially not possible.

In order to resolve this difficulty, and in accordance with the invention, a three-element electrode 10 is designed in which the three electrode elements 12*a*, 14*a* and 16*a*, (FIG. 2) and 12*b*, 14*b* and 16*b* (FIG. 3) are arranged symmetrically with respect to a rotational axis of symmetry (A) which extends perpendicular from the carrier 11 and, with respect to each other, the electrode elements are rotationally displaced.

Figure 2:
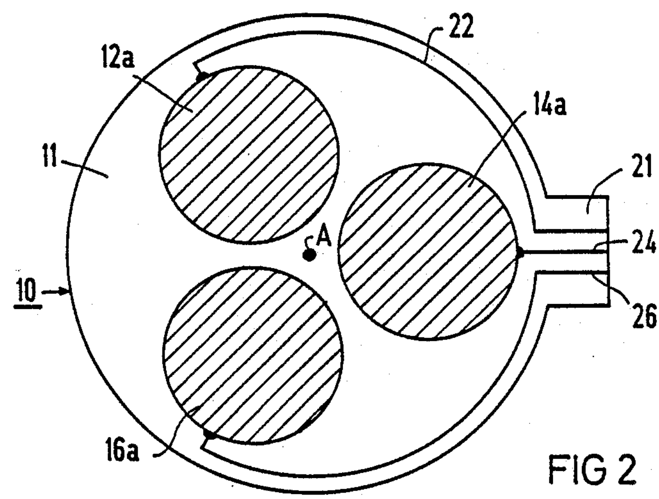
FIG. 2 illustrates a first embodiment of an electrode according to the invention with three symmetrically distributed circular electrode elements shown in perspective.

According to FIG. 2, three identical electrode elements 12*a*, 14*a* and 16*a*, which are fastened on a carrier 11 of flexible electrically insulating material, are of essentially circular shape. Each element includes a metal foil or metal netting. Carrier 11, which preferentially is self-adhesive and/or consists of a rubber, is likewise essentially circular. The external connecting wires of the three electrode elements 12*a*, 14*a* and 16*a* form essentially a triangular contact surface for the patient P. The electrode elements 12*a*, 14*a* and 16*a* are, thus, each displaced by 120° with respect to the axis of symmetry (A) in the circumferential direction with respect to each other. The axis (A) is central in and perpendicular to carrier 11.

At the right part of round carrier 11 a small support or link 21 for a wire connection is provided. This wire connection accepts three connecting wires 22, 24 and 26 for electrode elements 12, 14 and 16, respectively. As is evident, three wires 22, 24 and 26 are closely adjacent in the link and parallel to each other. It becomes thereby possible to permit a clamp to fasten around the link so as to establish a connection of three wires 22, 24 and 26 to safety circuit 18. In addition is noted that the two outer connecting wires 22 and 26 are of equal length, which simplifies their production and keeps the cost of storage down. Due to the equally long and symmetrical structure, identical parasitic capacitances are obtained and largely independent production tolerances result therefrom.

It should be pointed out that electrode elements 12*a*, 14*a*, and 16*a* in FIG. 2 are built with equal surface areas.

If the neutral electrode 10 illustrated in FIG. 2 is applied on the thigh of patient P (cf. FIG. 1), then it is largely irrelevant which positioning with respect to a rotation around the axis of symmetry (A) this takes place. In all positionings a largely uniform distribution of the HF energy onto the electrode elements 12*a*, 14*a* and 16 is achieved. The difference is maximally given by an angle of 60°. If more electrode elements are present, for example four instead of three, the differential angle becomes even smaller, for example 45°.

Figure 3:
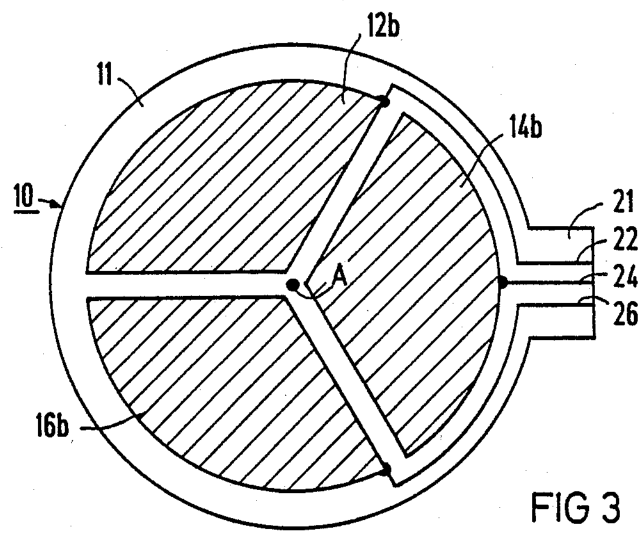
FIG. 3 illustrates a second embodiment of a neutral electrode according to the invention with three sector-shaped electrode elements shown in perspective.

In the embodiment of three-element electrode 10 according to FIG 3, a total of three sector-shaped electrode elements 12*b*, 14*b*, and 16b are arranged on the electrically insulating carrier 11. The three electrode elements 12*b*, 14*b* and 16*b* consist here of three circle-shaped sectors of equal size, with each sector having an angle of 120°. Hence, each electrode element has one curved and two straight edges. Here too, a rotationally symmetrical arrangement with respect to the axis of symmetry (A) which is perpendicular to the carrier 11, is provided. The angle of the rotational displacement here, too, is again 120°. This electrode 10 is also preferably self-adhesive.

With respect to the application of electrode 10 to the patient P, the same advantages are obtained here as were obtained with the electrode 10 of FIG. 2.

Thus, there has been shown and described novel multi-element neutral electrodes which fulfill all the objects and advantages sought therefore. Many changes, modifications, variations and other uses and applications of the subject invention will, however, become apparent to those skilled in the art after considering this specification and the accompanying drawings which disclose preferred embodiments thereof. For example, the rotational symmetry in the FIG. 2 and FIG. 3 embodiments were achieved by the electrode elements having at least partially uniformly curved circumferential lines. Further geometric forms of a multi-element electrode 10 with equally-sized or physiologically determined differently-sized electrode element surface areas 12, 14 and 16 are conceivable. The electrode 10 could also consist of four, five or six etc. elements, so that the angle of the rotational displacement of the discrete electrode elements in those cases, would be 90°, 72° or 60°, respectively, etc. All such changes, modifications, variations and other uses and applications which do not depart from the spirit and scope of the invention are deemed to be covered by the invention which is limited only by the claims which follow.

What we claim is:

1. Apparatus for performing electrosurgical procedures on the body of a patient, comprising:

a high frequency electrosurgical generator;

an active electrode coupled to said high frequency electrosurgical generator and adapted to make contact with a first portion of the body of said patient;

a neutral electrode including at least three electrode elements arranged on a common flexible carrier, said carrier including a link on a portion of its periphery on which connecting wires are run coupling said electrode elements to said high frequency electrosurgical generator, said electrode elements being adapted to make secure surface contact with a portion of the body of said patient which is remote from said first portion of said body; and a safety monitor circuit coupled to said neutral electrode via said carrier link for using the electrode elements of said neutral electrode as sensors for monitoring the sufficiency of surface contact between said electrode elements and the body of said patient, wherein:

for improving the operation of said neutral electrode as a sensor for said safety monitor circuit, at least a portion of each of said electrode elements has a uniformly-curved circumferential edge, said electrode elements are arranged so as to be symmetrically disposed with respect to an axis of symmetry of said carrier which extends perpendicularly from approximately the center of said carrier, and said electrode elements have equal surface areas and are arranged on said carrier so as to be displaced with respect to one another in a circumferential direction.

2. An electrode according to claim 1 wherein said electrode elements are round.

3. An electrode according to claim 1 wherein said electrode elements are sector-shaped.

4. An electrode according to claim 1 wherein said carrier is round.

* * * * *